(12) United States Patent  
Padgurskas et al.

(10) Patent No.: US 9,134,214 B2  
(45) Date of Patent: Sep. 15, 2015

(54) DEVICE FOR MEASURING THE INFLUENCE OF FRICTION FORCE ON WEAR CHARACTERISTICS OF A MATERIAL SURFACE WITH HIGH FREQUENCY LOADING FORCE

(71) Applicants: Juozas Padgurskas, Kauno .r (LT); Albinas Andriusis, Kaunas (LT)

(72) Inventors: Juozas Padgurskas, Kauno .r (LT); Albinas Andriusis, Kaunas (LT)

(*) Notice: Subject to any disclaimer, the term of this patent is extended or adjusted under 35 U.S.C. 154(b) by 556 days.

(21) Appl. No.: 13/663,173

(22) Filed: Oct. 29, 2012

(65) Prior Publication Data

US 2013/0047699 A1 Feb. 28, 2013

Related U.S. Application Data

(63) Continuation-in-part of application No. 12/919,672, filed as application No. PCT/LT2009/000003 on Feb. 25, 2009, now Pat. No. 8,297,104.

(30) Foreign Application Priority Data

Feb. 29, 2008 (LT) .................................. 2008 017

(51) Int. Cl.
*G01N 3/56* (2006.01)
*G01N 19/02* (2006.01)

(52) U.S. Cl.
CPC . *G01N 3/56* (2013.01); *G01N 19/02* (2013.01)

(58) Field of Classification Search
CPC ................................. G01N 19/02; G01N 3/56
See application file for complete search history.

(56) References Cited

U.S. PATENT DOCUMENTS

| | | | |
|---|---|---|---|
| 4,958,511 A | 9/1990 | Marcus | |
| 5,837,882 A | 11/1998 | Bacigalupo et al. | |
| 5,996,395 A | 12/1999 | Nagasawa et al. | |
| 6,412,330 B1 * | 7/2002 | Dicello et al. | 73/7 |
| 7,727,049 B2 * | 6/2010 | Benvegnu et al. | 451/5 |
| 2003/0101793 A1 * | 6/2003 | Evans | 73/9 |
| 2014/0298897 A1 * | 10/2014 | Leroux et al. | 73/150 R |

FOREIGN PATENT DOCUMENTS

| | | |
|---|---|---|
| JP | 2004039049 A | 2/2004 |
| SU | 86437 | 3/1949 |
| SU | 1174830 A1 | 8/1985 |

OTHER PUBLICATIONS

International Search Report from International Application No. PCT/LT 2009/000003 dated May 18, 2009 (1 page).
DGMK—Research Report 514, Hamburg, 1999. (12 pages).
English Abstract of SU-1174830-A1.
English Abstract of JP-2004039049-A.
English Abstract of SU-86437.

* cited by examiner

*Primary Examiner* — Lisa Caputo
*Assistant Examiner* — Punam Roy
(74) *Attorney, Agent, or Firm* — Patentagar PLLC; Alexander Rabinovich

(57) ABSTRACT

A device to measure the influence of friction force on wear characteristics of a material surface comprises a case with a cover. A moveable element (MFE) of a friction pair is fixed on a shaft installed in the case or is made flat. A holder of another, pressed, element of the friction pair (NMFE) and a clamp which applies a regulated load on the NMFE holder are attached to the cover. The NMFE is fixed to a NMFE holder installed using separate piezo sensors for pressing force and friction force in a sensor holder, which is installed using two pairs of lateral piezo actuators and their preload devices in an actuator holder, which is installed using two pairs of horizontal piezo actuators and their preload devices in the holder, which is installed in the cover of the device with membranes.

9 Claims, 1 Drawing Sheet

DEVICE FOR MEASURING THE INFLUENCE OF FRICTION FORCE ON WEAR CHARACTERISTICS OF A MATERIAL SURFACE WITH HIGH FREQUENCY LOADING FORCE

CROSS-REFERENCE TO RELATED APPLICATIONS

This application is a continuation-in-part of U.S. patent application Ser. No. 12/919,672 (publication US2011/0000278A1), which is a U.S. National phase application of the International application WO2009/108031 A1 (PCT/LT2009/000003) claiming priority to Lithuanian application 2008 17, filed Feb. 29, 2008, the three applications being hereby incorporated by reference in their entirety.

BACKGROUND OF THE INVENTION

1. Field of the Invention

The invention generally relates to the area of wear measurement of material surface. More specifically, it relates to a device for measuring the effect of friction force on wear characteristics of a material surface and can find its use in machinery production technology.

2. Description of Related Art

Surface wear depends on the contact geometry, static and dynamic loads of interacting surfaces, properties of materials of those surfaces, and lubricant properties. Various methods and devices have been used for measuring wear.

Known in the art is a device for measuring the influence of friction forces on wear characteristics of surface material when static or dynamic loads are applied (U.S. patent application 2011/0000278A1 assigned to the assignee of the present invention). The device comprises a frame with a cover. A shaft is installed in the frame. A moveable element of a friction pair is fixed on the shaft. Installed in the cover is a clamp which applies a variable load on the holder with the pressed friction element. However, the high-frequency loads cannot be properly applied on the friction pair of the device and consequently the high-frequency loads cannot be imitated reliably on the friction pairs.

BRIEF SUMMARY OF THE INVENTION

The device according to the present invention avoids the above mentioned disadvantages and adds possibility to load the sample using higher frequency force component and/or lateral vibrations. It is achieved by providing a device comprising a case with a cover, a friction pair of a moveable friction element and a pressed friction element, and a clamp in the cover for applying controlled force on the friction pair using a first force sensor. The moveable friction element is installed in the case, the non-movable (pressed) friction element is fixed to a holder mounted on a sensor holder via a second and a third sensors for pressing force and friction force, respectively. The sensor holder is attached to an actuator holder via first two pairs of lateral piezo actuators. The actuator holder is affixed to a holder via two pairs of horizontal piezo actuators. The holder is installed in the cover with membranes, whereby the clamp exerts pressure onto the holder through the first force sensor, holder, horizontal piezo actuators, actuator holder, lateral piezo actuators, sensor holder and second and third force sensors.

The reversible travel (rotational or linear) of the moveable friction element can be regulated, and the speed of the travel can be measured.

BRIEF DESCRIPTION OF THE DRAWINGS

Further objectives, features, characteristics, and effects of the invention will be clear from the ensuing detailed description of its illustrative embodiment and accompanying drawings in which.

DETAILED DESCRIPTION OF THE INVENTION

Figure 1:
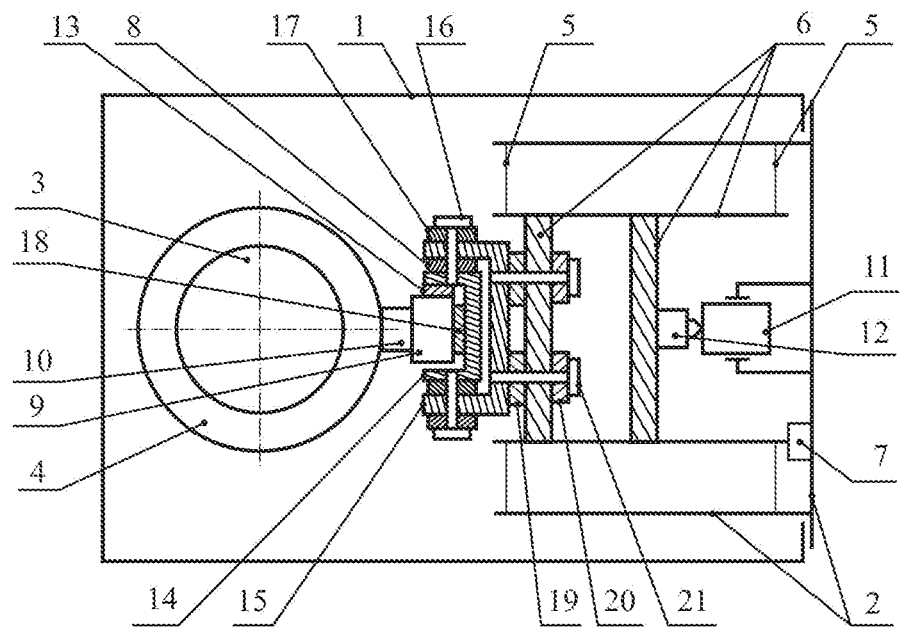
FIG. 1 illustrates in a sketch form the device according to the first embodiment of the present invention.
Figure 2:
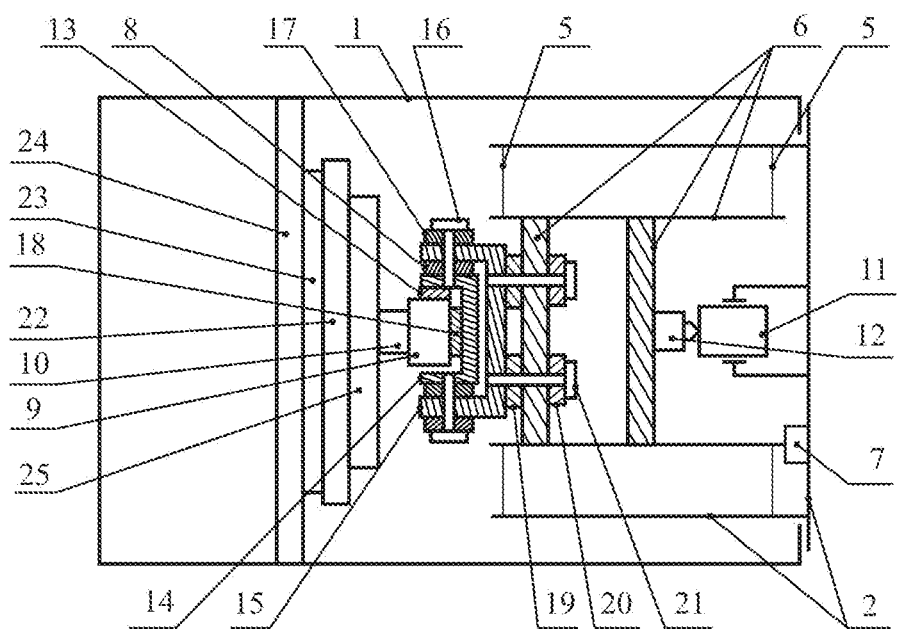
FIG. 2 shows in a sketch form the device according to the second embodiment of the present invention.

Referring now to FIGS. 1 and 2, the device of the present invention comprises a case 1 and a cover 2. According to the first embodiment (FIG. 1), a moveable friction element (MFE) 4 is affixed to the shaft 3 installed in the case 1. The MFE 4 and a non-movable (pressed) friction element (NMFE) 10 form a friction pair. The shaft 3 can be preferably rotated using an external motor (not shown). Alternatively, it can be rotated by piezo motor simulation using piezo actuators. Even further alternative is by using a controllable piezo actuator (not shown) in a NMFE to form a piezo motor of the friction pair A holder 6 is attached to the cover 2 with membranes 5 and interacts with the cover 2 through a shift sensor 7. An actuator holder 15 is mounted in the holder 6 with two pairs (only one pair is designated in FIG. 1) of piezo actuators 20, 19 and their preload devices 21 serving for a preliminary compression of the piezo actuators to enhance repeatability of the actuators. A sensor holder 14 is placed in the actuator holder 15 using two pairs (only one pair is designated in FIG. 1.) of piezo actuators 17 and 8 and their preload devices 16 also serving for a preliminary compression of the piezo actuators to enhance repeatability of the actuators. A NMFE holder 9 is installed in the sensor holder 14 with a pressing force higher frequency components piezo sensor 18 and a friction force piezo sensor 13. The NMFE holder 9 keeps the NMFE 10. A pressing force sensor 12 for the measurement of loading force is installed between the holder 6 and a clamp 11. The holder 6 interacts with the case 1 using a shift sensor 7 which is connected to a control board (not shown). The actuator holder 15 interacts with the holder 6 through two pairs of horizontal piezo actuators 19-20 connected to the control board. The sensor holder 14 interacts with the actuator holder 15 through two pairs of lateral piezo actuators 8-17 connected to the control board. The NMFE holder 9 interacts with the holder 6 through the piezo sensors for pressing force, 18, and friction force, 13, connected to the control board. The angle and speed of rotation of the shaft 3 can be measured and regulated, and the rotation can be reversed.

According to the second embodiment of the present invention (FIG. 2), a MFE 25 can be made flat and perform reciprocating motion relative the NMFE 10. In this embodiment, the MFE 25 is attached to a MFE holder 22 movable along a linear bearing 23 mounted on a bearing support 24 affixed to the case 1. The bearing 23 is preferably aerostatic to minimize friction losses. The movement of the MFE 25 can be reversible, and the speed and distance of the travel can be controlled and measured, the source of the movement being either an external linear motor or a piezo motor (not shown). Otherwise, elements of the device according to the second embodiment are same as those in the first embodiment (FIG. 1).

The device (of both embodiments) operates as follows. The MFE 4 (or 25) begins to travel (rotate (FIG. 1) or perform a linear movement (FIG. 2)) relative to the NMFE 10. Quasistatic pressing force and its variation regularity is programmed and controlled through the pressing force sensor 12, holder 6 and clamp 11. The horizontal vibration of the sample holder 9 can be generated using piezo actuators 20 and 19. Their controlled vibrations add a higher frequency component to the pressing force. The membranes 5 allow the holder 6 to move only along its axis (assumed to be horizontal in FIGS. 1 and 2 and not shown). The pressing force sensor 12 transfers to a control board a signal about relatively slow variation of the pressing force in the friction pair, i.e. between friction elements 4 (or 25) and 10. The friction force sensor 13 transfers a signal about the friction force. The lateral piezo actuators 8 and 17 generate lateral vibrations of the sensor holder 14. The piezo sensor 18 transfers to a control board a signal about higher frequency components of pressing force. The shift sensor 7 measures a shift of the holder 6 caused by wear of surfaces of the friction elements 4 (or 25) and 10.

The load (low frequency or quasi static) in the device is applied on the friction elements 4 (or 25) and 10 using the clamp 11 and can be modified using two pairs of piezo actuators 8 and 17 (a higher frequency lateral force component) and/or two pairs of piezo actuators 20 and 19 (a higher frequency pressing force component). The piezo actuators 8 and 17 are actuated simultaneously, but the actuator 17 is driven using phase inverted or phase-shifted driving signal as compared with the actuator 8 (or vice versa). The piezo actuators 20 and 19 are actuated simultaneously, but the actuator 19 is driven using phase inverted or phase-shifted driving signal relative to the actuator 20 (or vice versa).

The efficiency of the device is based on the absence of any interim chains which cause the raising lateral dynamic loads in the friction pair. The device of the present invention can operate without any interim chains (the U.S. patent application 2011/0000278A1) in case of switched off or supplied by direct current piezo actuators, because of their high stiffness. In case of driven piezo actuators, their influences on friction force and pressing force are controlled. The system of the membranes ensures the geometric stability of friction pair's contact and enables sustaining the settled regularity of the pressing force. The piezo actuators influence on stability is negligible, because of their low deformation amplitude.

It is to be understood that the above-described arrangement is merely illustrative of the application of the principles of the invention and that other arrangements may be devised by those skilled in the art without departing from the spirit of the invention. Specifically, the above-described elements of the device of this invention on the side of the NMFE 10 can be positioned movably attached to the case 1 rather than to the cover 2. It should be understood by those skilled in the art that various modifications, combinations, sub-combinations and alterations may occur depending on design requirements and other factors insofar as they are within the scope of the appended claims or the equivalents thereof.

What is claimed is:

1. A device for measuring the influence of friction force and load on wear characteristics of a material surface, the device comprising a case with a cover, a friction pair of a moveable friction element (MFE) and a non-movable pressed friction element (NMFE), and a clamp attached to the cover for applying controlled force on the friction pair using a first force sensor, the MFE being installed in the case, the NMFE being fixed to a NMFE holder mounted on a sensor holder via a second and a third sensors for pressing force and friction force, respectively, the sensor holder being attached to an actuator holder via two pairs of lateral piezo actuators, the actuator holder being affixed to a holder via pairs of horizontal piezo actuators, the holder being installed in the cover with membranes, whereby the clamp exerts pressure onto the NMFE holder through the first force sensor, holder, horizontal piezo actuators, actuator holder, lateral piezo actuators, sensor holder and second and third force sensors.

2. The device according to claim 1, wherein the MFE is fixed on a shaft, whose rotation speed is regulable.

3. The device according to claim 1, wherein the MFE is fixed on the shaft, whose rotation speed is measured.

4. The device according to claim 1, wherein the MFE is made flat and attached to a MFE holder adapted to move linearly.

5. The device according to claim 1, wherein the piezo actuators are driven using inverted phase, phase shifted or direct current signals.

6. A device for measuring the influence of friction force and load on the wear characteristics of a material surface, the device comprising a case with a cover, a friction pair of a moveable friction element (MFE) and a non-movable pressed friction element (NMFE), a clamp for applying controlled force on the friction pair using a first force sensor, the MFE being fixed on a shaft, whose rotation speed is regulated, installed in the case, the NMFE being fixed to a NMFE holder, the NMFE holder being fixed on a sensor holder using a second and a third sensors for pressing force and friction force, respectively, the sensor holder being fixed to an actuator holder using two pairs of lateral piezo actuators, the actuator holder being fixed to a holder using two pairs of horizontal piezo actuators, the holder being installed with membranes in the cover, to thereby exert pressure from the clamp onto the NMFE holder through the first force sensor, holder, horizontal piezo actuators, actuator holder, lateral piezo actuators, sensor holder and second and third force sensors.

7. The device for measuring the influence of friction force and load on wear characteristics of a material surface comprising:
   a case with a cover,
   a friction pair of a moveable friction element (MFE) and a non-movable pressed friction element (NMFE),
   a NMFE holder, holding the NMFE, and
   a clamp for applying a controlled force on a friction pair,
   the NMFE holder being installed with piezo sensors for pressing force and friction force connected to a sensor holder,
   the sensor holder being installed with piezo actuators connected to an actuator holder,
   the actuator holder being installed with membranes in the cover interacting with the cover through a shift sensor,
   the MFE being made flat, attached to the case, and adapted to move linearly,
   the clamp exerting pressure onto the NMFE through a holder,
   a pressing force sensor installed between the clamp and the holder,
   force sensors installed between the sample holder and the sensor holder,
   two pairs of lateral piezo actuators being installed between the sensor holder and actuator holder, and
   two pairs of horizontal piezo actuators installed between the actuator holder and holder.

8. The device according to claim 7, wherein the attachment of the MFE to the case is made through a MFE holder interacting with a linear bearing attached to a bearing support affixed to the case.

9. The device according to claim 7, wherein the linear travel of the MFE is made reversible and regulable.

* * * * *